United States Patent
Atthoff et al.

(10) Patent No.: US 9,763,670 B2
(45) Date of Patent: Sep. 19, 2017

(54) COMPRESSION UNIT AND A RADIAL ARTERY COMPRESSION SYSTEM

(75) Inventors: Björn Atthoff, Uppsala (SE); Erik Hansson, Uppsala (SE); Fredrik Preinitz, Uppsala (SE); Fredrik Mahlin, Uppsala (SE)

(73) Assignee: ST. JUDE MEDICAL COORDINATION CENTER BVBA, Zaventem (BE)

( * ) Notice: Subject to any disclaimer, the term of this patent is extended or adjusted under 35 U.S.C. 154(b) by 596 days.

(21) Appl. No.: 13/522,638

(22) PCT Filed: Jan. 19, 2011

(86) PCT No.: PCT/SE2011/050059
§ 371 (c)(1),
(2), (4) Date: Jul. 17, 2012

(87) PCT Pub. No.: WO2011/090429
PCT Pub. Date: Jul. 28, 2011

(65) Prior Publication Data
US 2012/0296369 A1    Nov. 22, 2012

Related U.S. Application Data

(60) Provisional application No. 61/296,226, filed on Jan. 19, 2010.

(30) Foreign Application Priority Data

Jan. 19, 2010 (SE) ...................................... 1050059

(51) Int. Cl.
    *A61B 17/00*    (2006.01)
    *A61B 17/132*   (2006.01)
    (Continued)

(52) U.S. Cl.
CPC ...... *A61B 17/1322* (2013.01); *A61B 17/1325* (2013.01); *A61B 17/135* (2013.01);
(Continued)

(58) Field of Classification Search
CPC .............. A61B 17/135; A61B 17/1322; A61B 17/1325; A61B 17/1327; A61B 17/1355;
(Continued)

(56) References Cited

U.S. PATENT DOCUMENTS

RE7,896 E  *  9/1877  Lubin ........................ 128/111.1
2,045,750 A     6/1936  Buschenfeldt
(Continued)

FOREIGN PATENT DOCUMENTS

EP    1 295 564 B1    3/2003
JP    2-109603 U      9/1990
(Continued)

OTHER PUBLICATIONS

Japanese Office Action, dated May 20, 2014, 6 pgs.

*Primary Examiner* — Jonathan Miles
*Assistant Examiner* — Kankindi Rwego
(74) *Attorney, Agent, or Firm* — Foley & Lardner LLP (57) ABSTRACT

The invention relates to a compression unit adapted to be arranged around a patient's forearm to provide pressure to a radial artery puncture site, wherein the compression unit comprises a unit attachment band provided with a frame, and a compression element in the shape of an inflatable bladder, the compression element is further adapted to be arranged within said frame, such that when the compression unit is arranged around a patient's forearm, the compression element provides pressure to the puncture wound when the compression element is inflated. The invention also relates to a radial artery compression system.

23 Claims, 7 Drawing Sheets

(51) Int. Cl.
*A61B 17/135* (2006.01)
*A61B 17/22* (2006.01)

(52) U.S. Cl.
CPC . *A61B 17/1327* (2013.01); *A61B 2017/00557* (2013.01); *A61B 2017/00902* (2013.01); *A61B 2017/00907* (2013.01); *A61B 2017/22059* (2013.01)

(58) Field of Classification Search
CPC .............. A61B 17/0057; A61B 17/132; A61B 17/12009; A61B 2017/12004; A61F 2013/0028; A61F 5/0118; A61F 5/3723; A61F 5/3738; A61F 5/3761; A61F 2/2481; A61H 39/04; A61H 2205/027; A61H 2205/067; A61H 2201/0103; A61H 2201/1635; A61H 2003/006
USPC .............. 606/201, 202, 203, 204; 602/1–79; 128/877–879
See application file for complete search history.

(56) References Cited

U.S. PATENT DOCUMENTS

| | | | |
|---|---|---|---|
| 2,529,786 A | 11/1948 | Shaw | |
| 4,520,806 A | 6/1985 | Miller | |
| 4,798,199 A | 1/1989 | Hubbard et al. | |
| 5,269,803 A | 12/1993 | Geary et al. | |
| 5,464,420 A | 11/1995 | Hori et al. | |
| 5,486,194 A * | 1/1996 | Kawasaki et al. | 606/203 |
| 5,514,155 A | 5/1996 | Daneshvar | |
| 5,601,597 A | 2/1997 | Arrowood et al. | |
| 5,695,520 A | 12/1997 | Bruckner et al. | |
| 6,283,126 B1 * | 9/2001 | Jessen | A61F 5/37 128/878 |
| 6,647,986 B1 | 11/2003 | Korotko et al. | |
| 7,498,477 B2 | 3/2009 | Wada et al. | |
| 8,945,173 B2 | 2/2015 | Atthoff et al. | |
| 2004/0039413 A1 | 2/2004 | Akerfeldt et al. | |
| 2006/0190026 A1 * | 8/2006 | Sanders | A61H 39/04 606/204 |
| 2006/0211987 A1 | 9/2006 | Williams | |
| 2009/0131780 A1 | 5/2009 | O'Connor et al. | |
| 2009/0138039 A1 * | 5/2009 | Wada | A61B 17/1325 606/202 |

FOREIGN PATENT DOCUMENTS

| | | |
|---|---|---|
| JP | 2001-061845 A | 3/2001 |
| JP | 2004-237004 A | 8/2004 |
| NL | 1016025 C2 | 3/2002 |
| WO | WO 91/05525 A1 | 5/1991 |
| WO | WO 96/25110 A1 | 8/1996 |
| WO | WO 2004/017841 A1 | 3/2004 |
| WO | WO 2008/013107 A1 | 1/2008 |

* cited by examiner

FIG. 16

COMPRESSION UNIT AND A RADIAL ARTERY COMPRESSION SYSTEM

FIELD OF THE INVENTION

The present invention relates to a radial artery compression unit and to a radial artery compression system including a radial artery compression unit, with which a compression force is applied on the radial artery such that haemostasis can be obtained.

BACKGROUND OF THE INVENTION

To access a patient's vascular system for an invasive medical procedure such as catheterization or similar procedures, a puncture is made in e.g. the femoral artery or the radial artery. The present invention is related to radial artery procedures. Following an invasive medical procedure, such as catheterisation or similar in medical procedure, the flow of blood through the puncture wound has to be stopped, so that haemostasis can begin as soon and fast as possible after the completion of the invasive medical procedure. Several devices have been suggested that facilitate and accelerate this haemostasis by providing a compression pressure that compresses blood vessels in various parts of the body to stop the flow of blood therethrough.

In the case of radial artery catheterisation, several radial artery occluders have been developed that stop the flow of blood through the puncture wound in the wrist by applying a compression force that occludes the radial artery.

One example of such a pressure-applying device is known from U.S. Pat. No. 5,601,597. This known artery occluder comprises a wrist splint, an adjustable securing strap attached to one end of the splint, and an adjustable pressure strap attached to the other end of the splint and provided with a pressure pad.

U.S. Pat. No. 6,647,986 shows a hand/wrist positioning splint to keep the hand positioned for radial artery access and to permit application of a haemostasis band. Two straps are used to secure the patient's hand to the splint and the haemostasis band comprises buckles to apply sufficient pressure to the puncture site.

Another example of a pressure-applying device is known from U.S. Pat. No. 7,498,477, disclosing a haemostatic device with an inflatable balloon. A main balloon is pressed against a puncture site of a patient and filled with a first fluid to inflate the balloon. A pressing member is further provided on the main balloon, and when filled with a second fluid, it presses against the main balloon to apply a compressive force to the puncture site that acts ht an inclined direction with respect to the surface of the limb of the patient. The main balloon and die pressing member are held in place against the puncture site with a flexible band and a curved plate.

From WO 96/25110 a further device for compression of an artery is known. The device comprises an elongated compression element, a pressure distribution and support plate and strap means for holding the compressing element and the pressure distribution plate in place.

It is an object of the invention to provide an improved device that enables an accurately applied pressurization against a puncture site, and in particular enables a following adjustment of the applied pressure to the puncture site.

It is a further object of the invention to provide an improved device which is more hygienic than prior art devices, and that is economical to manufacture and ship to the end user.

SUMMARY OF THE INVENTION

The above-mentioned objects are achieved by means of a compression unit adapted to be arranged around a patient's forearm to provide pressure to a radial artery puncture site, and a radial artery compression system comprising a dorsal forearm plate and a compression unit, according to the independent claims.

According to one aspect the present invention relates to a compression unit adapted to be arranged around a patient's forearm to provide pressure to a radial artery puncture site, wherein the compression unit comprises a unit attachment band provided with a frame, and a compression element in the shape of an inflatable bladder, the compression element is further arranged within the frame, such that when the compression unit is arranged around a patient's forearm, the compression element provides pressure to the puncture wound when the inflatable bladder is inflated. The inventive compression unit provides for a continuous adjustment of the pressure to the puncture site by inflating the bladder when the compression unit is arranged around a patient's forearm, and thereby an accurately applied pressure against the puncture site where a following adjustment of the applied pressure is possible.

According to another aspect, the invention relates to a radial artery compression system, comprising a compression unit and a dorsal forearm plate provided with a distal and a proximal attachment band adapted to attach the dorsal forearm plate at the dorsal forearm of a patient, wherein the compression unit s adapted to be arranged around a patient's forearm where the dorsal forearm plate is attached and fixated, such that the compression element provides pressure to a radial artery site.

The dorsal forearm plate fixates the wrist in a controlled position minimizing bleeding complications and is comfortable for the patient and slimmer than previously used plates. In addition, the plate prevents the patient from flexing, the wrist and causing late bleedings as well as reduces the risk of venous stasis.

The primary use for a radial artery compression system according to the present invention is to achieve hemostasis after a transradial procedure. However, with the dorsal forearm plate, the cardiologist may also use the plate pre-, during and post procedure to fixate the wrist in a flexed position which allows easier access to the radial artery. The dorsal forearm plate further distributes reaction force over the dorsal side of the forearm to avoid building up a local maximum pressure on the forearm which might give venous stasis.

The unit attachment band provides for a compression unit which is more hygienic than prior art devices, as the compression unit is in one part that can be separated from the system by means of the unit attachment band and exchanged or separately sterilized. The band is advantageously adjustable to it different sizes of forearms.

Preferred embodiments are set forth in the dependent claims and in the detailed description.

SHORT DESCRIPTION OF THE APPENDED DRAWINGS

Below the invention will be described in detail with reference to the appended figures, of which:

in FIGS. 11-13.

DETAILED DESCRIPTION OF PREFERRED EMBODIMENTS OF THE INVENTION

Figure 1:
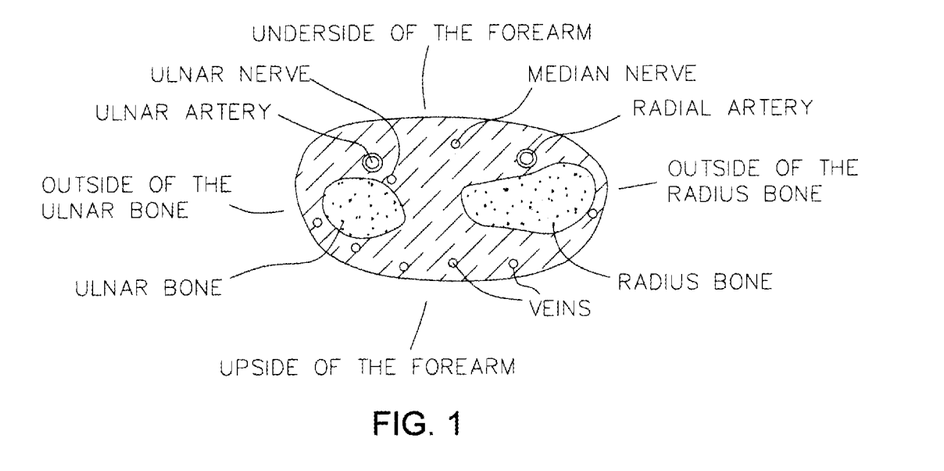
FIG. 1 is a schematic cross-sectional view of the wrist anatomy.
Figure 2:
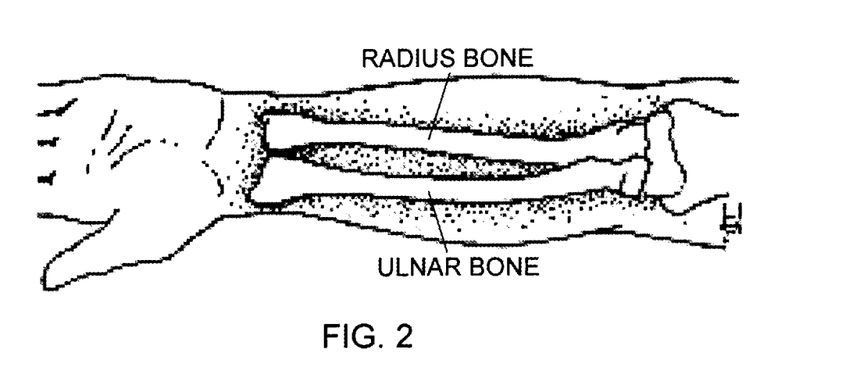
FIG. 2 shows schematically the forearm bones, the ulnar bone and the radius bone.

As background information, FIG. 1 shows schematically in cross-section the wrist anatomy with the ulnar and radius bones, the ulnar and radius arteries, the ulnar and median nerves, and the superficial veins at the upside of the forearm. In the description below, several references are made to different sides of the forearm, and also these terms are indicated in FIG. 1. FIG. 2 shows schematically the forearm bones, the ulnar bone and the radius bone, of the left forearm.

Figure 3:
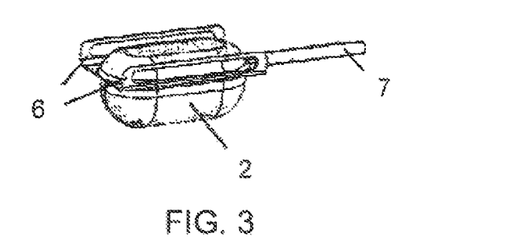
FIG. 3 shows a compression unit according to one embodiment of the invention.
Figure 8:
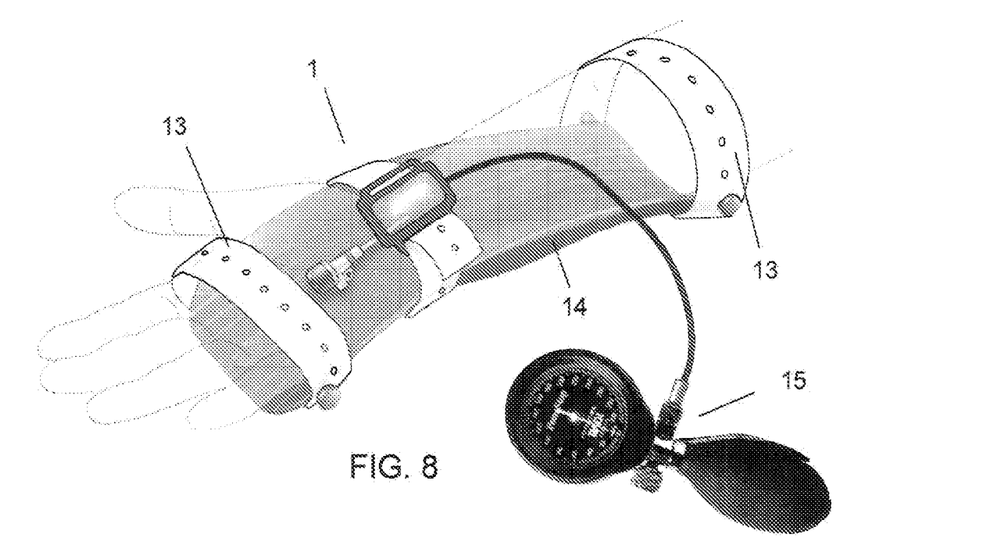
FIG. 8 is a perspective view of a radial compression system according to one embodiment of the invention.
Figure 9:
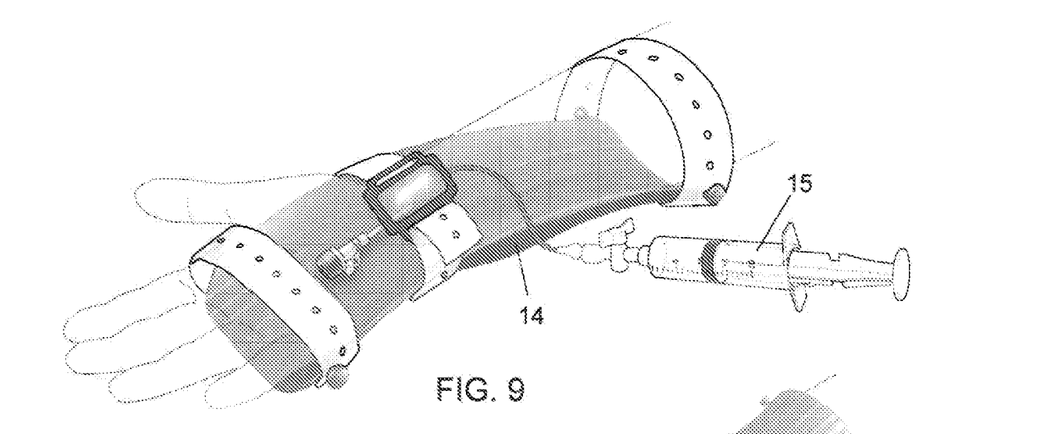
FIG. 9 is a perspective view of a radial compression system according to another embodiment of the invention.

FIG. 3 shows a compression unit 1 comprising a unit attachment band 3 provided with a frame 4, and a compression element 2 in the shape of an inflatable bladder. By means of the unit attachment band 3, the compression unit 1 may be arranged around a patient's forearm to provide pressure to a radial artery puncture site as illustrated in FIGS. 8 and 9. The compression element 2 is farther adapted to be arranged within the frame 4, such that when the compression unit 1 is arranged around the patient's forearm, the compression element 2 provides pressure to the puncture wound when the compression element 2 is inflated.

In the figures the compression element 2 is shown in an inflated state, but it is understood that the compression element 2 may have different shapes dependent on which material the compression is made of and how much the compression element 2 is inflated.

The frame 4 may be of any shape enabling the compression element 2 to be arranged within and attached to the frame 4. In the figures, the frame 4 has an essentially rectangular shape to be able to apply pressure longitudinally along an artery, but could instead be e.g. essentially quadratics. Regarding the thickness of the frame 4, the frame 4 preferably has a thickness withstanding the pressure that is built up when the compression element 2 is inflated, thus, the frame 4 should preferably not bend when the compression element 2 is inflated. The width of the frame 4 is according to one embodiment approximately 2-4 mm.

The frame 4 is further a stabilizing unit which provides support for the compression element 2 when the compression element 2 is attached to the frame 4 and inflated, such that the pressure can be focused against a puncture wound.

The compression element 2 is advantageously adapted to be attached to the frame 4 by means of at least one mechanical joint. From the FIGS. 3 to 7, it can be seen that the compression unit 1 comprises bladder attachment means 6 in the shape of loops on the outside of the compression element 2, and the frame 4 comprises frame attachment means 5 adapted to mate with the loops for holding the compression element 2 in place in the frame 4. One of the frame attachment means 5 is, according to one embodiment, part of the unit attachment band 3, and one of the loops is adapted to be threaded over the unit attachment band 3 to attach the compression element 2 to the frame 4. The other one of the frame attachment means 5 is according to one embodiment a protruding part of the compression element 2. One loop is then adapted to be threaded over the protruding part to attach the compression element 2 to the frame 4. Other kinds of frame attachment means 5 e.g. in the shape of hooks are also possible embodiments.

According to another embodiment, the compression element 2 is attached to the frame 4 by means of gluing or welding.

In the figures, the compression element 2 has an elongated extension, defining a longitudinal axis of the element, in the direction of an artery to which it is to be applied. According to one embodiment, the compression element 2 comprises a first pan 9 adapted to face a puncture wound, and an opposite second part 10. The parts 9, 10 are according to one embodiment made of two equally sized films and are attached to each other along their edges, e.g. by welding, to form an inflatable bladder. The bladder attachment means 6 are advantageously made from the same films by providing appropriate sized loops in the films, and the bladder attachment means 6 and the first and second parts 9, 10 may thus be made of the same material. The bladder is preferably attached to the frame 4 by means of the attachment means when it is substantially not inflated, and when the bladder thereafter is inflated, the bladder attachment means 6 here in the shape of loops are tightened to the frame 4 against the bladder, advantageously against a middle line of the bladder, such that the bladder is securely and firmly attached to the frame 4. Each of the parts preferably has a concave inner side and a convex outer side forming an inflatable bladder when attached to each other and inflated. The compression element 2 may thus be formed in other ways, e.g. by moulding. When the bladder is not inflated, the first part 9 and the second part 10 are according to one embodiment, of the same size. According to one embodiment, the first part 9 and the second part 10 are made of non-elastic material, i.e. rigid material. The bladder will then provide for a focused pressure over the puncture wound when the bladder is in use and inflated and also when the pressure in the bladder is increased, as the first par 9 becomes rounded against the wrist and presses in a longitudinal line following the artery in which a puncture wound has been made.

According to another embodiment, the first part 9 and the second part 10 are made of elastic material. If elastic material is used and the compression unit 1 is attached to a patient with a certain tension in the unit attachment band 3, inflation of the bladder will mainly result in an increased pressure area of the compression element 2 against the puncture wound, instead of an increased pressure locally over the artery. This is thus an advantage if an increased pressure area is desired e.g. it the puncture wound is large in size, or if it is desired to improve the distribution of the pressure. If the parts are made of materials with different elasticity, the parts may expand differently when the inflatable bladder is inflated. As can be seen from the FIGS. 3 and 4, the compression element 2, i.e. the inflatable bladder, is inflated, and the first part 9 is at least partly made of a material with a higher elasticity than the second part 10, which allows the first part 9 of the inflatable bladder to expand more than the second part 10, and then to provide a pressure against the puncture site of a forearm when the compression element 2 is arranged within the frame 4 and the compression unit 1 comprising the compression element 2 in its turn is attached around the forearm. The second part 10 in the figures is thus made of a material with a lower elasticity than the first part 9, and according to one embodiment the second part 10 is made of a material with an elasticity that essentially does not allow the second part 10 to expand. When the inflatable bladder then is inflated, the bladder is essentially only expanding against the puncture site when in use, thus enabling a controlled pressurization of the puncture site. The first and second parts 9, 10 may also have different elasticity to give necessary strength to the bladder attachment means 6. Thus, the second part 10 may have a strength that enables the bladder attachment means 6 to be rigidly attached to the frame 4 without e.g. bending the bladder attachment means 6. The bladder attachment means 6 may be attached to the compression element 2 along the dividing line between the first and second parts 9, 10, e.g. by welding or gluing.

According to one embodiment, the first part 9 and the second part 10 are injection-moulded. The first part 9 may be injection-moulded of a thermoplastic elastomer, preferably transparent, and the second part 10 may be injection-moulded of a rigid plastic material, preferably also transparent. The first part 9 of the thermoplastic elastomer is then adapted to face a puncture wound of a patient. According to one embodiment, the compression element 2 is injection-moulded of a thermoplastic elastomer in one piece. The thermoplastic elastomer may be transparent, thus, the compression element 2 is then transparent.

If the inflatable bladder comprises pets made of materials with the same elasticity and the same thickness, they will expand essentially symmetrically when inflated.

The first part 9 may be of a material which gives certain desired properties against the skin of a patient, such as a gentle feeling or friction.

The inflatable bladder is according to one embodiment made of polyethylene terephthalate film, ethylene vinyl acetate film, polyurethane film or any other kind of weldable plastic. The compression element 2 i.e. the inflatable bladder is preferably made from a transparent material, thereby providing the possibility of direct visual observation of the puncture wound, which facilitates the positioning of the compression element 2.

Figure 6:
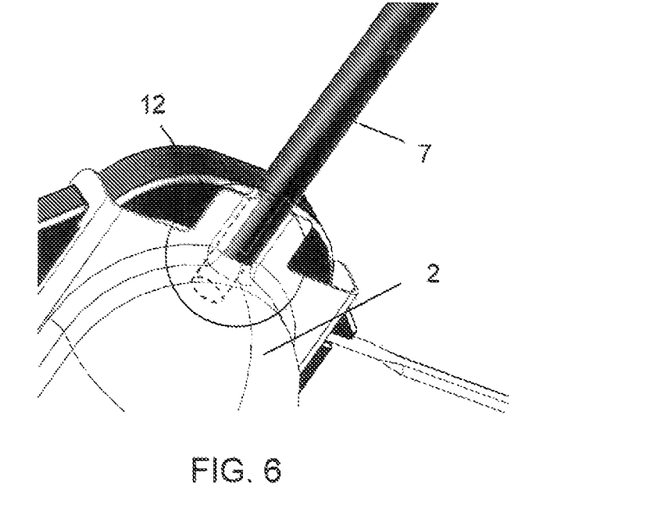
FIG. 6 shows a connection between the compression element in the shape of an inflatable bladder and a tube for inflation of the bladder according to one embodiment of the invention.
Figure 7:
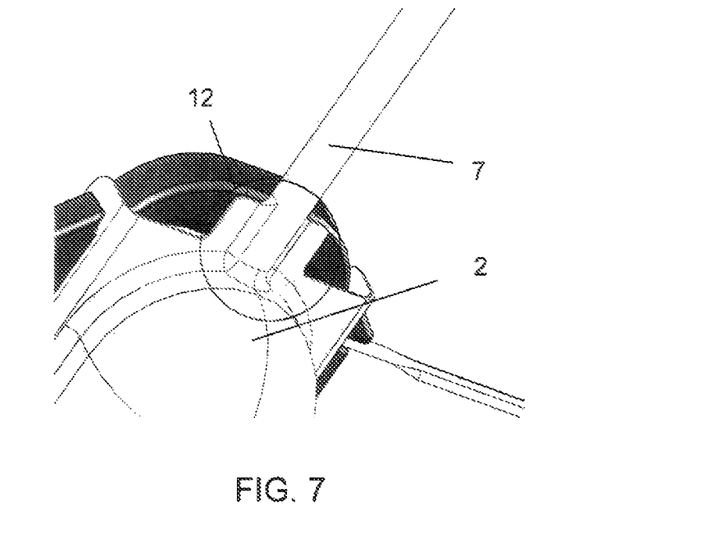
FIG. 7 shows a connection between the compression element in the shape of an inflatable bladder and a tube for inflation of the bladder according to one embodiment of the invention.

To be able to inflate the compression element 2 it comprises a fluid connection 12 adapted to be connected to a tube 7 for inflation of the compression element 2. Two different embodiments are illustrated in FIGS. 6 and 7, wherein the fluid connection 12 in FIG. 6 is in the shape of an elongated channel serving, as a filling tube 7. Another tube 7 may then be threaded over the elongated channel to inflate the compression element 2. In the end of the fluid connection 12 a valve that can be closed and opened, e.g. a stopcock, a check-valve or similar may be provided to open a fluid-channel between the compression element 2 and a pressurizing unit 15. The fluid connection 12 in FIG. 7 is in the shape of a tube 7 welded to the compression element 2. The compression element 2 may be inflated and pressurized by means of a pressurizing unit 15 as illustrated in FIGS. 8 and 9. In FIG. 8, the pressurizing unit 15 is a manometer adapted to indicate the pressure in the compression element 2. In FIG. 9, the pressurizing unit 15 is an injector adapted to indicate the pressure in the compression element 2. The fluid used for inflating the compression element 2 is preferably air or gas, but according to another embodiment the fluid is a liquid such as a physiological saline solution. An advantage with using a liquid is that if the inflatable bladder breaks, e.g. if the first part 9 is scratched by a needle and breaks such that fluid escapes from the bladder, then liquid leaks to the wound, and not air or gas which may be more dangerous for the patient. When using air or gas, the pressure is thus mostly more easily adjusted compared to using a liquid.

Figure 4:
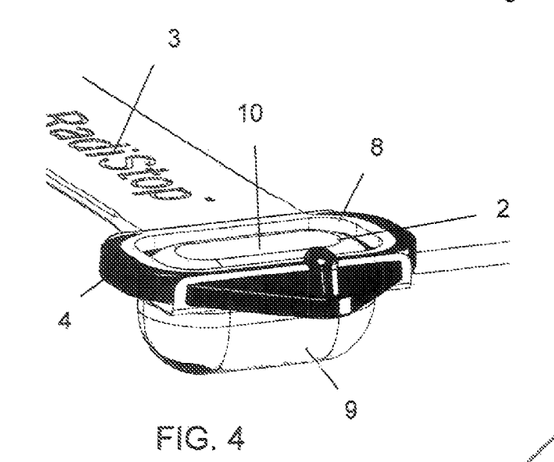
FIG. 4 shows an enlarged view of a part of the compression unit according to one embodiment of the inventio.
Figure 5:
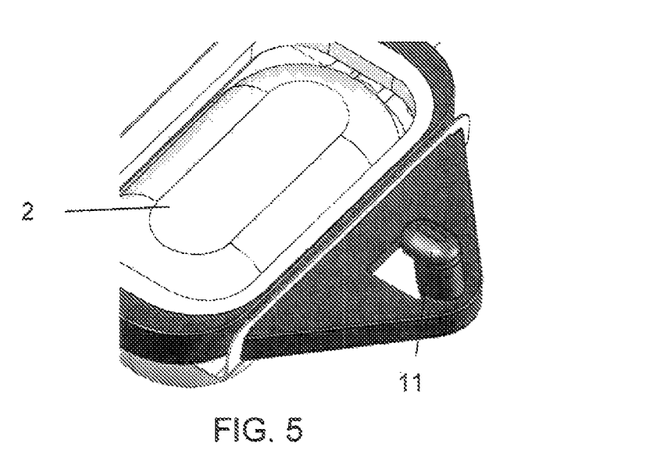
FIG. 5 shows another enlarged view of the compression element according to one embodiment of the invention.

The unit attachment band 3 is according to one embodiment fixated to one side of the frame 4. According to another embodiment, the hand is fixated to the frame 4 by means of an inner frame 8 adapted to fit inside the frame 4 wherein the compression element 2 is arranged as can be seen in FIGS. 3 and 4. The band is in turn attached to the inner frame 8.

The unit attachment band 3 is preferably flexible. The compression unit 1 may be rigidly attached to the arm of the patient by the unit attachment bands 3 provided with Velcro tape. The unit attachment band 3 may instead be provided with holes and the frame 4 provided with a mating attachment knob 11 therefore. Regarding material, the band may be made from e.g. a thermoplastic elastomer.

Figure 10:
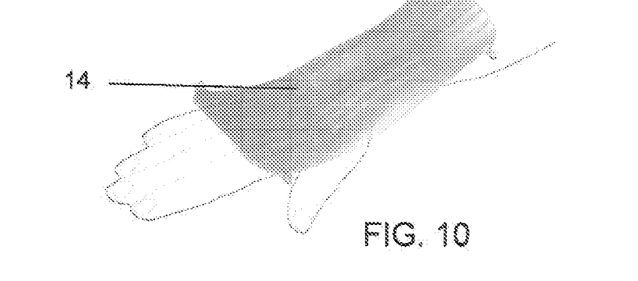
FIG. 10 is a perspective view of the radial compression system seen from the dorsal side of the forearm.

The invention also relates to a radial artery compression system as illustrated in inter alia FIGS. 8 and 9. The system comprises a compression unit 1 as explained above, and a dorsal forearm plate 14 provided with a distal and a proximal attachment band 13, adapted to attach the dorsal forearm plate 14 at the dorsal forearm of a patient, wherein the compression unit 1 is adapted to be arranged around a patient's forearm where the dorsal forearm plate 14 is attached and fixated, such that the compression element 2 provides pressure to a radial artery site. The hands are preferably flexible. In FIG. 10 the system without the compression unit 1 is seen from the underside of the forearm.

Figure 11:
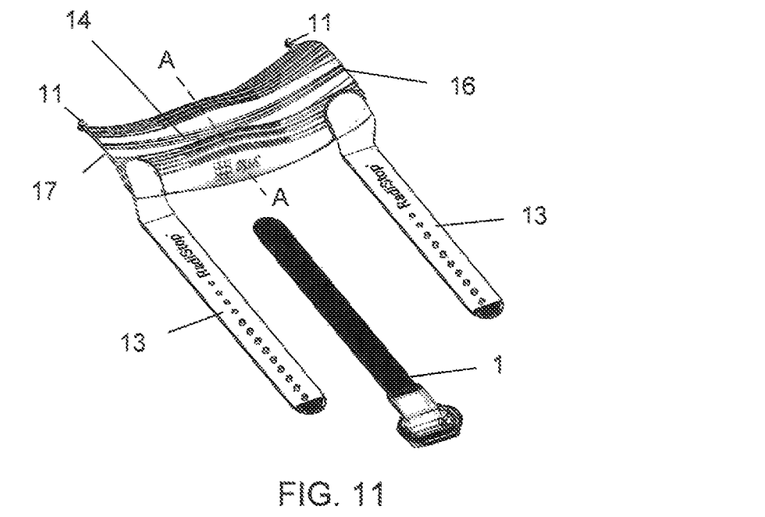
FIG. 11 is a perspective view of the radial compression system according to a further embodiment of the present invention.
Figure 12:
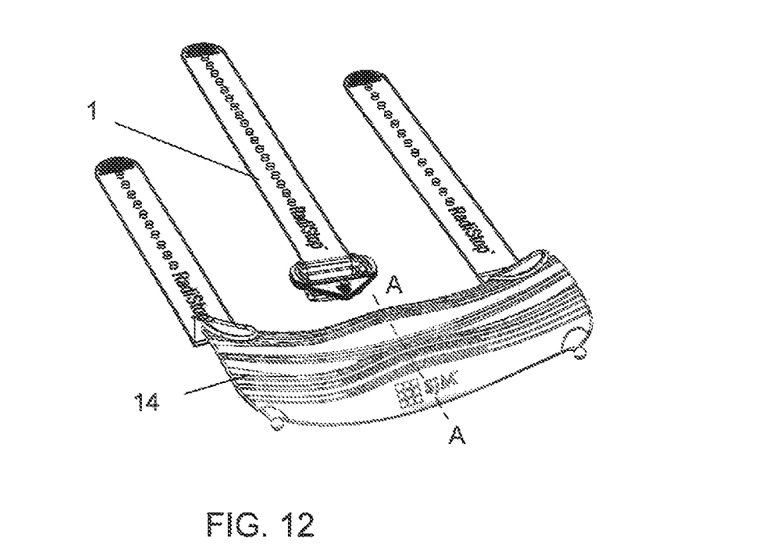
FIG. 12 is a perspective view of the radial compression system according to a still further embodiment of the present invention.

FIGS. 11 and 12 show a dorsal forearm plate 14 having a three-dimensional concave shape adapted to the shape of the dorsal forearm such that the dorsal forearm may rest on the forearm plate. The dorsal forearm plate 14 has an essentially rectangular extension having opposing long sides and opposing short sides 16, 17 and has a substantially rigid unitary body adapted to underlie the posterior of the patient's hand, wrist and forearm. An exemplary width of the plate may be 6-9 cm and the length is in the interval of 15-23 cm. Naturally different sizes of the plate may be available, smaller ones to children and larger to adults and obese patients.

In the figure can be seen that the shape of the side of the plate is adapted to face the forearm during use and it is also adapted to the anatomy of the forearm in that it comprises two elongated depressions 18 running in the longitudinal direction of the plate. These two depressions 18 are intended to, during use of the plate, accommodate the tartar bone and radius bone of the patient, in particular the distal parts of these bones, the so called styloid processes of each bone, in the respective depression 18. Furthermore, an elongated ridge 19, formed between the depressions 18, is adapted to extend into the softer tissue between the bones in order to orient and stabilize the forearm when attached to the plate.

Figure 13:
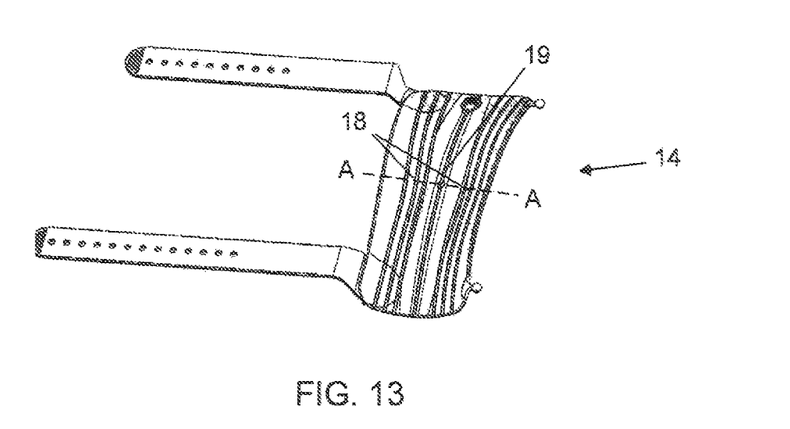
FIG. 13 is a perspective view showing the side facing the patients forearm of the dorsal forearm plate according to the invention.

FIG. 13 is a perspective view showing the side facing the patient's forearm of the dorsal forearm plate 14 according to the invention.

Figure 14:
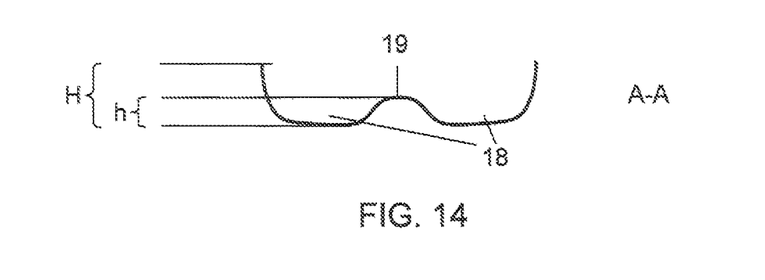
FIG. 14 is a schematic cross-sectional view of the dorsal forearm plate according to the present invention along A-A indicated e.g.

In order for the patient to comfortably rest and orient the forearm on the dorsal forearm plate 14 the height of the elongated ridge 19 at a cross-section A-A, essentially at a midpoint of the plate in the longitudinal direction, is at a level being in the interval of 10-50% of the total height of the plate at said cross-section A-A. The cross-section A-A is depicted e.g. in FIGS. 11-13. The height of the ridge 19 is indicated as "h" in FIG. 14 and may be in the interval 5-15 mm and more specifically 6-9 mm, and the total height is indicated "H" which may be in the interval of 15-30 mm.

The dorsal forearm plate 14 may be rigidly attached to the arm of the patient by the attachment hands 13 provided with Velcro tape. The attachment bands 13 may also be provided with holes and the plate provided with mating attachment knobs 11 therefore. In the latter case, the bands are preferably made at least partly of an elastic material to ensure a comfortable fit.

The dorsal forearm plate 14 is essentially arc-shaped in the longitudinal direction such that it only rests on its short sides 16, 17 when arranged on a plane surface. Each of the short sides 16, 17 has an essentially straight supporting edge along a major part of its length and the supporting edges of said short sides 16, 17 are arranged in the same virtual plane. Thereby the plate has a stable support when used on a flat surface, e.g. a table. When the plate lays on a flat surface the midpoint of the plate is about 1 cm above the surface.

Figure 15:
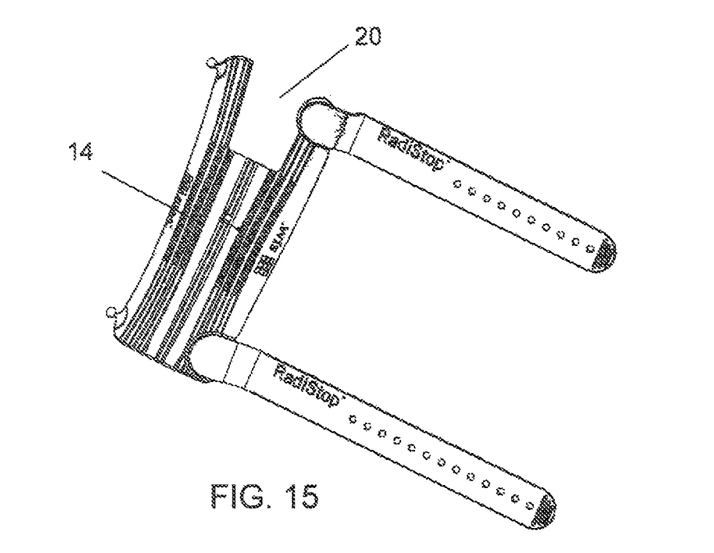
FIG. 15 is a perspective view from below of the dorsal forearm plate according to an alternative embodiment.
Figure 16:
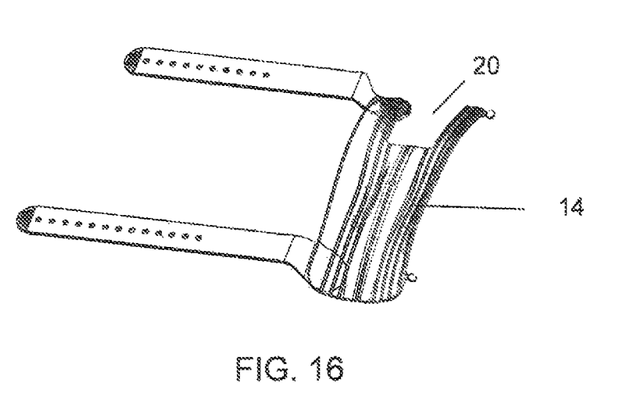
FIG. 16 is a perspective view from the side facing the patient's forearm of the dorsal forearm plate according to an alternative embodiment of the invention.

In order to e.g. gain access to blood vessels at the dorsal side of the hand the dorsal forearm plate 14 is provided with a recess 20 extending from the distal short side 16 extending in the proximal direction such that an opening, having an essentially rectangular shape, is provided in the plate. This recess 20 is shown in FIG. 15. FIG. 16 is a perspective view from the side facing the patient's forearm of the dorsal forearm plate 14 according to the alternative embodiment.

The surface not intended to face the forearm of the plate is provided with a texture such that the friction is high and that said high friction surface extends at least along the mid third part of the plate.

Regarding the material of the dorsal forearm plate 14 it may be made from pressure moulded plastic or any other suitable material that stabilizes the forearm. Preferred materials are polypropylene or polycarbonate. The attachment bands 13 are preferably made from a thermoplastic elastomer.

When the forearm of the patient is readily fixed in the dorsal forearm plate 14 by the attachment bands 13 the puncture can be made for e.g. an interventional procedure of choice. When the desired procedure(s) are completed, the flow of blood from the puncture wound is stopped by applying the compression element 2 to the puncture wound. Thereby, the blood flow is stopped directly and efficiently.

The present invention is not limited to the above-described preferred embodiments. Various alternatives, modifications and equivalents may be used. Therefore, the above embodiments should not be taken as limiting the scope of the invention, which is defined by the appending claims.

REFERENCE LIST

1 Compression unit
2 Compression element
3 Unit attachment band
4 Frame
5 Frame attachment means
6 Bladder attachment means
7 Tube
8 inner frame
9 First part
10 Second part
11 Knob
12 Tube/fluid connection
13 Attachment band
14 Dorsal forearm plate
15 Pressurizing unit
16 Distal short side
17 Proximal short side
18 Depression
19 Ridge
20 Recess

The invention claimed is:

1. A compression unit configured to be arranged around a patient's forearm to provide pressure to a radial artery puncture site, comprising:
a unit attachment band provided with a frame, and
a compression element that comprises an inflatable bladder,
wherein the compression element is further arranged within and bounded by the frame such that a side of the inflatable bladder facing away from the radial artery puncture site is uncovered and exposed through the frame, such that when the compression unit is arranged around the patient's forearm, the compression element provides pressure to the radial artery puncture site when the inflatable bladder is inflated,
wherein the compression element is attached to the frame by at least one mechanical joint, and
wherein the at least one mechanical joint comprises at least one loop attached to the outside of the inflatable bladder, and the frame comprises a protruding part configured to pass through the at least one loop to hold the compression element in place within the frame.

2. A radial artery compression system, comprising:
a compression unit configured to be arranged around a patient's forearm to provide pressure to a radial artery puncture site, further comprising
a unit attachment band provided with a frame, and
a compression element that comprises an inflatable bladder,
wherein the compression element is further arranged within and bounded by the frame such that a side of the inflatable bladder facing away from the radial artery puncture site is uncovered and exposed through the frame, such that when the compression unit is arranged around the patient's forearm, the compression element provides pressure to the radial artery puncture site when the inflatable bladder is inflated, and
a dorsal forearm plate provided with a distal and a proximal attachment band, configured to attach the dorsal forearm plate at the dorsal forearm of the patient and fixate the patient's wrist in a flexed position, wherein the compression unit is configured to be arranged around the patient's forearm where the dorsal forearm plate is attached and fixed, such that the compression element provides pressure to the radial artery puncture site, the dorsal forearm plate further comprising a three-dimensional concave shape configured to the shape of the dorsal forearm such that the dorsal forearm may rest on the dorsal forearm plate, an essentially rectangular extension having opposing long sides and opposing short sides, and a substantially rigid unitary body configured to underlie the posterior of the patient's hand, wrist and forearm, wherein a shape of a side of the dorsal forearm plate is further configured to face the forearm during use, and further comprises two elongated depressions running in a longitudinal direction of the dorsal forearm plate such that, during use of the dorsal forearm plate, the ulnar bone and radius bone of the patient rest in a respective depression, and an elongated ridge, formed between the two elongated depressions, is configured to extend into the softer tissue between the bones in order to orient and stabilize the forearm when attached to the plate.

3. The radial artery compression system according to claim 2, wherein the frame has an essentially rectangular shape.

4. The radial artery compression system according to claim 2, wherein the compression element has an elongated extension, defining a longitudinal axis of the element, parallel to a longitudinal direction of an artery to which the compression element is to be applied.

5. The radial artery compression system according to claim 2, wherein the compression element is attached to the frame by at least one mechanical joint.

6. The radial artery compression system according to claim 2, wherein the compression element is glued or welded to the frame.

7. The radial artery compression system according to claim 2, wherein the inflatable bladder comprises a first part configured to face the radial artery puncture site, and an opposite second part, wherein the first part and the second part are attached to each other.

8. The radial artery compression system according to claim 7, wherein the first part and the second part are made of elastic material.

9. The radial artery compression system according to claim 8, wherein the first part and the second part are at least partly made of materials with different elasticity.

10. The radial artery compression system according to claim 7, wherein the first part and the second part are made of non-elastic material.

11. The radial artery compression system according to claim 2, wherein the compression element comprises a tube connection configured to be connected to a tube for inflation of the inflatable bladder.

12. The radial artery compression system according to claim 2, wherein the compression element is made from a transparent material, thereby providing the possibility of direct visual observation of the radial artery puncture site, which facilitates the positioning of the compression element.

13. The radial artery compression system according to claim 2, wherein the unit attachment band is fixed to the frame.

14. The radial artery compression system according to claim 13, wherein the unit attachment band is provided with hook-and-loop fasteners used to attach the unit to the arm of the patient.

15. The radial artery compression system according to claim 13, wherein the unit attachment band is provided with holes and the frame is provided with a mating attachment knob.

16. The radial artery compression system according to claim 2, wherein a height of the elongated ridge at a cross-section located essentially at a midpoint of the dorsal forearm plate in the longitudinal direction is at a level being in the interval of 10-50% of a total height of the dorsal forearm plate at the cross-section.

17. The radial artery compression system according to claim 2, wherein the attachment bands are provided with hook-and-loop fasteners used to attach the dorsal forearm plate to the arm of the patient.

18. The radial artery compression system according to claim 2, wherein the attachment bands are provided with holes and the dorsal forearm plate is provided with mating attachment knobs.

19. The radial artery compression system according to claim 2, wherein the dorsal forearm plate is essentially arc shaped in the longitudinal direction such that it rests only on its short sides when arranged on a plane surface, and that each of the short sides has an essentially straight supporting edge along a major part of its length and the supporting edges of the short sides being arranged in the same virtual plane.

20. The radial artery compression system according to claim 2, wherein the dorsal forearm plate is provided with a recess extending from the distal short side extending in the proximal direction such that an opening, having an essentially rectangular shape, is provided in the dorsal forearm plate, so as to gain access to blood vessels at the dorsal side of the hand.

21. The radial artery compression system according to claim 2, wherein a surface of the dorsal forearm plate not intended to face the forearm is provided with a texture such that the friction is high and that the high friction surface extends at least along the mid third part of the dorsal forearm plate.

22. The radial artery compression system according to claim 2, wherein the dorsal forearm plate is made from pressure moulded plastic.

23. A compression unit configured to be arranged around a patient's forearm to provide pressure to a radial artery puncture site, comprising:

a unit attachment band provided with a frame, and a compression element that comprises an inflatable bladder, wherein the compression element is further arranged within and bounded by the frame such that a side of the inflatable bladder facing away from the radial artery puncture site is uncovered and exposed through the frame, such that when the compression unit is arranged around the patient's forearm, the compression element provides pressure to the radial artery puncture site when the inflatable bladder is inflated, and wherein the compression element further comprises a protruding part disposed at one end of the frame, a first loop attached to an outside of the inflatable bladder and configured to hold the unit attachment band, and a second loop attached to the outside of the inflatable bladder and configured to hold the protruding part to attach the inflatable bladder to the frame.

* * * * *